United States Patent
Li et al.

(10) Patent No.: US 6,316,621 B1
(45) Date of Patent: Nov. 13, 2001

(54) TRIETHYLENEDIAMINE PRODUCTION USING PHOSPHATE CATALYSTS

(75) Inventors: Hong-Xin Li, Lansdale; Lenore Ann Emig, Whitehall; Richard Paul Underwood, Allentown, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/533,431

(22) Filed: Mar. 23, 2000

Related U.S. Application Data

(62) Division of application No. 09/316,609, filed on May 21, 1999, now abandoned.

(51) Int. Cl.[7] .............................................. C07D 295/023
(52) U.S. Cl. ................................................................ 544/352
(58) Field of Search ............................................... 544/352

(56) References Cited

U.S. PATENT DOCUMENTS

| | | | |
|---|---|---|---|
| 3,297,701 | | 1/1967 | Brader et al. ............... 260/268 |
| 4,405,784 | * | 9/1983 | Wells ........................... 544/352 |
| 4,514,567 | * | 4/1985 | Wells ........................... 544/352 |
| 4,521,600 | * | 6/1985 | Wells et al. .................. 544/352 |
| 4,695,661 | * | 9/1987 | Homann et al. ............. 568/903 |
| 4,757,143 | | 7/1988 | Vanderpool et al. ........ 544/352 |
| 5,037,838 | * | 8/1991 | Zimmerman et al. ....... 544/352 |
| 5,118,651 | * | 6/1992 | Gubelmann et al. ........ 502/202 |
| 5,162,531 | * | 11/1992 | King ............................ 544/352 |

FOREIGN PATENT DOCUMENTS 5-17461 * 1/1993 (JP) .

* cited by examiner

*Primary Examiner*—Mark L. Berch
*Assistant Examiner*—Thomas C. McKenzie
(74) *Attorney, Agent, or Firm*—Mary E. Bongiorno

(57) ABSTRACT

A new method of making phosphate-based catalysts by mixing phosphoric acid with a substantially water insoluble alkaline earth metal salt such that the phosphorus to alkaline earth metal molar ratio is less than 1. The product, containing alkaline earth metal hydrogen phosphate and the starting alkaline earth metal salt, is filtered and dried. The product can be used as a catalyst in the production of triethylenediamine from, for example, mono- and di-substituted piperazines, such as hydroxyethylpiperazine and aminoethylpiperazine, ethanolamines and substituted ethanolamines, and crude hydroxyethylpiperazine containing piperazine, hydroxyethylpiperazine, bis-hydroxyethylpiperazine, and water.

6 Claims, No Drawings

TRIETHYLENEDIAMINE PRODUCTION USING PHOSPHATE CATALYSTS

CROSS-REFERENCE TO RELATED APPLICATIONS

This is a divisional of application Ser. No. 09/316,609, filed on May 21, 1999, now abandoned.

BACKGROUND OF THE INVENTION

Organic synthesis by condensation reactions resulting in the loss of a molecule of water or of ammonia is well known in the art. Certain of such reactions are generally effected in the presence of acidic catalysts. An important area in which such acid catalysis has been employed is in cyclization reactions as in the synthesis of triethylenediamine and its C-substituted homologues. The catalysts are typically solid products of the Lewis acid type.

One group of catalysts which have been found to be effective for acid catalyzed organic condensation reactions such as those used to produce triethylenediamine (also referred to herein as TEDA) are phosphate catalysts. The following patents provide examples of such phosphate catalysts.

U.S. Pat. No. 3,297,701 (Brader et al., 1967) discloses the use of metal phosphate catalysts such as aluminum phosphate, calcium phosphate and cobalt phosphate, for synthesis of TEDA and C-substituted TEDA from piperazines or alkanolamines.

U.S. Pat. No. 4,405,784, U.S. Pat. No. 4,514,567, and U.S. Pat. No. 4,521,600 (Wells et al, 1983–1985) disclose the use of strontium monohydrogen phosphate ($SrHPO_4$), strontium pyrophosphate ($Sr_2P_2O_7$), strontium dihydrogen phosphate ($Sr(H_2PO_4)_2$), the pyrophosphate, monohydrogen phosphate and dihydrogen phosphate of copper, magnesium, calcium, barium, zinc, aluminum, lanthanum, cobalt, nickel, cerium and neodymium, and mixtures thereof, as effective catalysts for organic condensation reactions especially the reaction to form TEDA. The catalysts are made by reacting a soluble salt of one of the metals with the mono- or diphosphate of an alkali metal or ammonium. The pH of the reaction mixture is adjusted to 5±3 in order to precipitate out the mono- or dihydrogen phosphate of the metal.

U.S. Pat. No. 4,757,143 (Vanderpool et al, 1988) discloses the conversion of cyclic and acyclic hydroxyethyl ethylenepolyamines to TEDA using a catalyst composed of zirconia or titania to which from 0.5 to about 7 wt % of phosphorous has been thermally chemically bonded in the form of phosphate linkages.

U.S. Pat. No. 5,037,838 (Zimmerman et al, 1991) discloses the conversion of N-hydroxyethyl piperazine to TEDA using a titania-supported tungstopyrophosphate catalyst.

BRIEF SUMMARY OF THE INVENTION

This invention is directed to a new method of making phosphate-based catalysts which are useful for the production of triethylenediamine (TEDA). The catalysts are prepared by mixing phosphoric acid with a substantially water insoluble alkaline earth metal salt such that the phosphorus to alkaline earth metal molar ratio is less than 1. An aqueous slurry of the salt, such as strontium carbonate, calcium carbonate, or barium carbonate, is mixed with an aqueous solution of phosphoric acid to form an alkaline earth hydrogen phosphate. Since less than stoichiometric amounts of alkaline earth metal salt and acid are used, some of the alkaline earth metal salt remains unreacted and is present in the precipitated product. The product, containing alkaline earth metal hydrogen phosphate and the starting alkaline earth metal salt, is filtered and dried. The mixture can be used as a catalyst in the production of TEDA from, for example, mono- and di-substituted piperazines, such as hydroxyethylpiperazine and aminoethylpiperazine, ethanolamines and substituted ethanolamines, and crude hydroxyethylpiperazine containing piperazine, hydroxyethylpiperazine, bis-hydroxyethylpiperazine, and water.

There are several advantages to this method of making the alkaline earth metal hydrogen phosphate compared to the known method of reacting an alkaline earth metal nitrate with sodium hydrogen phosphate, both of which are in solution:

the alkaline earth metal salt does not need to be put into solution before reacting it with phosphoric acid;

the catalyst does not need to be washed to remove unwanted metals such as sodium; and the cost of the raw materials is much lower.

It has also been found that the product made by the method of this invention has much better activity and selectivity in making TEDA from hydroxyethylpiperazine than catalysts formed from a known method.

DETAILED DESCRIPTION OF THE INVENTION

Preparation of alkaline earth metal hydrogen phosphates can be carried out by first forming an aqueous slurry of an alkaline earth metal salt which is substantially insoluble in water, such as strontium carbonate, barium carbonate, or calcium carbonate. By "substantially insoluble in water" is meant that the solubility in water at ambient temperature (i.e., approximately 25° C.) is less than 1 part per 100 parts water.

An aqueous solution of phosphoric acid, for example, an 85% aqueous solution, is added to the alkaline earth metal salt slurry, with stirring, in an amount that the molar ratio of phosphoric acid to alkaline earth metal salt is less than 1; preferably less than 0.8. The reaction can be carried out at ambient temperature, i.e., approximately 25° C., and atmospheric pressure.

The product precipitate is a mixture of the alkaline earth metal hydrogen phosphate salt and unreacted alkaline earth metal salt. The molar ratio of phosphorous to alkaline earth metal in the product is less than 1; preferably, less than 0.8. The precipitate is filtered and can then be washed, for example with water, although washing is not required. The filtered precipitate can then be dried.

For use as a catalyst, the product may be employed in the form of irregular particles of a desired size range by breaking up the washed and dried filter cake or in the form of regular shaped pellets obtained by known methods of casting, pelletizing or extruding. The product may also be deposited or otherwise impregnated into the pores of a microporous substrate such as alumina, silica, silica-alumina, and the like.

In using the catalyst of the present invention to catalyze organic condensation reactions, substantially the same conditions may be employed as when using known catalysts. For optimum results, however, some adjustment in temperature, diluent, and/or space rate may be found beneficial.

A continuous process is typically used in the production of the triethylenediamine. The temperature range is about 285 to 420° C., preferably 300 to 390° C., the pressure range is about 0.1 to 1.5 atmospheres (101.4 to 152.03 kPa), preferably 0.3 to 1.0 atm (30.3 to 101.4 pKa), and the liquid hourly space velocity (LHSV) of organic feedstock per volume of catalyst is in the range of about 0.05 to 1.5, preferably 0.1 to 0.3.

The reaction an be carried out in the presence of an inert gas such as nitrogen, argon or helium.

In the preparation of TEDA, the organic feedstock includes mono- and di-substituted piperazines selected from the group consisting of hydroxyethylpiperazine, aminoethylpiperazine, ethanolamines, and substituted ethanolamines. The catalysts of this invention are relatively uneffected by the purity of the feedstock. For example, high conversion and good yields can be obtained from crude hydroxyethylpiperazine containing, in addition to the hydroxyethylpiperazine, piperazine, bis-hydroxyethylpiperazine, and water.

The invention will be further clarified by a consideration of the following examples, which are intended to be purely exemplary of the invention.

EXAMPLE 1

PREPARATION OF CATALYST

A slurry was prepared by adding 30.1 g of $SrCO_3$ (supplied by CPC) to 40.02 g of de-ionized water. To this slurry, 11.6 g of 85% phosphoric acid was added with stirring. Carbon dioxide was released during the reaction. The solid was filtered, washed with de-ionized water, and dried at 110° C. The solid contained a mixture of $SrHPO_4$ and $SrC_3$. Chemical analysis showed that the solid had a P/Sr ratio of 0.54. The BET surface area was 6 $m^2/g$.

EXAMPLE 2

PREPARATION OF TEDA FROM HYDROXYETHYL PIPERAZINE USING A CATALYST PREPARED FROM STRONTIUM CARBONATE

The reactions was carried out in a continuous flow, tubular reactor under atmospheric pressure. The catalyst of Example 1, pelletized to 18–35 mesh particles, was loaded into the reactor and heated to 340° C. under dry nitrogen flow. An aqueous solution of 25% hydroxyethyl piperazine (HEP) was pumped into the reactor at 1.5 ml/min. Nitrogen was co-fed into the reactor at 22 ml/min. Reaction effluent was collected and analyzed by gas chromatograph. Results are shown in the table below.

EXAMPLE 3

PREPARATION OF TEDA FROM HYDROXYETHYL PIPERAZINE USING A CATALYST PREPARED FROM STRONTIUM CARBONATE

The catalyst was prepared as in Example 1 except that the $SrCO_3$ was supplied by Aldrich. TEDA was prepared according to the procedure of Example 2. Results are shown in the table below.

EXAMPLE 4

PREPARATION OF TEDA FROM HYDROXYETHYL PIPERAZINE USING A CATALYST PREPARED FROM CALCIUM CARBONATE

The catalyst was prepared according to the procedure of Example 1 except that calcium carbonate was used instead of strontium carbonate. TEDA was prepared according to the procedure of Example 2. Results are shown in the table below.

COMPARATIVE EXAMPLE 5

PREPARATION OF STRONTIUM HYDROGEN PHOSPHATE BY A PRIOR ART PROCESS AND USE OF THE CATALYST IN TEDA SYNTHESIS

A strontium hydrogen phosphate catalyst was prepared according to the procedure of U.S. Pat. No. 4,405,784 in which a solution of strontium nitrate $(Sr(NO_3)_2)$ was reacted with sodium hydrogen phosphate $(Na_2HPO_4)$ and the pH of the reaction mixture was adjusted to about 5.5. The product was removed by filtration, washed with water, and dried. The catalyst was used in the production of TEDA according to the procedure of Example 2. Results are shown in the table below.

| Ex. | Catalyst | Reactants for Forming Catalyst | Hours on Stream | % HEP Converted | TEDA wt % | Piperazine wt % | Other wt % |
|---|---|---|---|---|---|---|---|
| 2 | $SrHPO_4$/ $SrCO_3$ P/Sr = 0.5 BET = 6 $m^2/g$ | $SrCO_3$ (CPC) + 85% $H_3PO_4$ | 30 | 80.3 | 82.7 | 4.7 | 12.6 |
| 3 | $SrHPO_4$/ $SrCO_3$ P/Sr = 0.5 BET = 6.9 $m^2/g$ | $SrCO_3$ (Aldrich) + 85% $H_3PO_4$ | 50 | 84.9 | 85.5 | 4.5 | 10.0 |
| 4 | $CaHPO_4$/ $CaCo_3$ P/Ca = 0.5 BET = 17 $m^2/g$ | $CaCO_3$ (Aldrich) + 85% $H_3PO_4$ | 30 | 82.7 | 83.4 | 7.4 | 9.3 |
| 5 | $SrHPO_4$ P/Sr = 1 BET = 9 $m^2/g$ | $Sr(NO_3)_2$ + $Na_2HPO_4$ | 48 | 66.7 | 73.1 | 4.8 | 22.1 |

Reaction conditions: 1.0 cc catalyst (18–35 mesh); temperature = 340° C.; pressure = 1 atm; feed = 1.5 ml/h of 25 wt % HEP; nitrogen flow = 22 cc/min.

Data for examples 2, 3, and 4, in which a mixture of alkaline earth metal hydrogen phosphate and carbonate were used, compared to example 5, in which pure strontium hydrogen phosphate was used, show that use of the catalyst of this invention unexpectedly resulted in higher conversion of hydroxyethylpiperazine to TEDA and higher selectivity to TEDA. In addition, the higher conversion and higher selectivity of catalyst of this invention was achieved with lower amounts of the strontium or calcium hydrogen phosphate. The data of examples 2, 3 and 4 also show that improved conversion and selectivity were obtained over a wide range of catalyst surface area; i.e., $6m^2/g$ to $17\ m^2/g$.

What is claimed is:

1. A method for preparing triethylenediamine comprising contacting, under reaction conditions sufficient to produce triethylenediamine, a compound selected from the group consisting of hydroxyethylpiperazine, crude hydroxyethylpiperazine, N-aminoethyl piperazine, and ethanolamines, with a catalyst comprising a combination of an alkaline earth metal hydrogen phosphate and an alkaline earth metal salt wherein the molar ratio of phosphorus to alkaline earth metal in the combination is less than 1, said catalyst prepared by combining an aqueous phosphoric acid solution with an aqueous slurry of a substantially insoluble alkaline earth metal salt such that the molar ratio of phosphoric acid to alkaline earth metal salt is less than 1, to form a precipitate of the alkaline earth metal hydrogen phosphate containing residual alkaline earth metal salt, and filtering and drying the precipitate.

2. The method of claim 1 wherein the molar ratio of phosphorous to alkaline earth metal is in the combination of less than 0.8.

3. A method for preparing triethylenediamine comprising contacting, under reaction conditions sufficient to produce triethylenediamine, a compound selected from the group consisting of hydroxyethylpiperazine, crude hydroxyethylpiperazine, N-aminoethyl piperazine, and ethanolamines, with a catalyst comprising a combination of an alkaline earth metal hydrogen phosphate and a carbonate salt of strontium, calcium, or barium, wherein the molar ratio of phosphorus to alkaline earth metal in the combination is less than 1.

4. The method of claim 3 wherein the compound is hydroxyethlpiperazine or crude hydroxyethylpiperazine.

5. The method of claim 3 wherein the compound is crude hydroxyethylpiperazine.

6. The method of claim 3 wherein the ratio of phosphorous to alkaline earth metal in the combination is 0.8.

* * * * *

UNITED STATES PATENT AND TRADEMARK OFFICE
CERTIFICATE OF CORRECTION

PATENT NO.    : 6,316,621 B1
DATED         : November 13, 2001
INVENTOR(S)   : Hong-Xin Li, Lenore Ann Emig and Richard Paul Underwood It is certified that error appears in the above-identified patent and that said Letters Patent is hereby corrected as shown below:

<u>Column 6,</u>
Line 19, delete the first word "hydroxyethlpiperazine" and substitute therefore
-- hydroxyethylpiperazine --.

Signed and Sealed this

Thirtieth Day of September, 2003

JAMES E. ROGAN
*Director of the United States Patent and Trademark Office*